United States Patent
Moriya et al.

(10) Patent No.: US 9,066,831 B2
(45) Date of Patent: Jun. 30, 2015

(54) ABSORBENT ARTICLE WITH PRESSED GROOVES OVERLYING A COMPRESSED REGION AND METHOD OF MANUFACTURING THE SAME

(75) Inventors: Ayako Moriya, Kagawa (JP); Yusuke Kawakami, Kagawa (JP)

(73) Assignee: Unicharm Corporation, Ehime (JP)

( * ) Notice: Subject to any disclaimer, the term of this patent is extended or adjusted under 35 U.S.C. 154(b) by 359 days.

(21) Appl. No.: 13/581,114

(22) PCT Filed: Feb. 23, 2011

(86) PCT No.: PCT/JP2011/053940
§ 371 (c)(1),
(2), (4) Date: Oct. 19, 2012

(87) PCT Pub. No.: WO2011/105413
PCT Pub. Date: Sep. 1, 2011

(65) Prior Publication Data
US 2013/0035656 A1    Feb. 7, 2013

(30) Foreign Application Priority Data
Feb. 26, 2010   (JP) .................................. 2010-043533

(51) Int. Cl.
*A61F 13/47* (2006.01)
*A61F 13/475* (2006.01)
*A61F 13/533* (2006.01)
(Continued)

(52) U.S. Cl.
CPC .......... *A61F 13/4704* (2013.01); *A61F 13/4756* (2013.01); *A61F 13/539* (2013.01); *A61F 13/15707* (2013.01);
(Continued)

(58) Field of Classification Search
CPC ............ A61F 13/4704; A61F 13/4756; A61F 13/4758; A61F 13/49001; A61F 13/533; A61F 13/536; A61F 13/51108; A61F 2013/4587; A61F 2013/51078; A61F 2013/53739; A61F 13/15707; A61F 13/539; A61F 2013/53734; A61F 2013/53778
USPC ................................... 604/378–380, 385.101
See application file for complete search history.

(56) References Cited

U.S. PATENT DOCUMENTS 3,908,659 A * 9/1975 Wehrmeyer et al. .......... 604/374
5,795,344 A * 8/1998 Chappell ...................... 604/379
(Continued)

FOREIGN PATENT DOCUMENTS

DE    297 24 125 U1    7/2000
EP    2 087 866 A1     8/2009
(Continued)

OTHER PUBLICATIONS

Official Action and English translation from corresponding Japanese Application No. 2010-043533 dated Aug. 21, 2013 (5 pgs).
(Continued)

*Primary Examiner* — Tan-Uyen (Jackie) T Ho
*Assistant Examiner* — Kathryn E Ditmer
(74) *Attorney, Agent, or Firm* — Brinks Gilson & Lione (57) ABSTRACT

An absorbent article having a compressed region formed by a compressing process in an absorption layer on a side facing to the backsheet; and a plurality of pressed grooves are formed by a pressing process in the absorption layer on a side facing to the topsheet, within a region opposed to the compressed region.

6 Claims, 7 Drawing Sheets (51) Int. Cl.
   *A61F 13/539* (2006.01)
   *A61F 13/15* (2006.01)
   *A61F 13/537* (2006.01)

(52) U.S. Cl.
   CPC ............. *A61F 2013/53734* (2013.01); *A61F 2013/53778* (2013.01); *A61F 2013/15439* (2013.01)

(56) References Cited

U.S. PATENT DOCUMENTS

| | | | |
|---|---|---|---|
| 6,177,605 B1 * | 1/2001 | Trombetta et al. | 604/378 |
| 6,563,013 B1 * | 5/2003 | Murota | 604/380 |
| 2005/0118399 A1 * | 6/2005 | Perneborn | 428/171 |
| 2008/0119810 A1 * | 5/2008 | Kuroda et al. | 604/379 |

FOREIGN PATENT DOCUMENTS

| | | |
|---|---|---|
| JP | H06-245951 A | 9/1994 |
| JP | 2005-160702 | 6/2005 |
| JP | 2005-312547 A | 11/2005 |
| JP | 2006-115996 A | 5/2006 |
| JP | 2007-089818 A | 4/2007 |
| JP | 2008125918 A * | 6/2008 |
| WO | WO 98/27908 | 7/1998 |

OTHER PUBLICATIONS

International Search Report based on corresponding PCT application No. PCT/JP2011/053940 filed May 24, 2011 (3 pgs).
Japanese Official Action and English translation from corresponding Japanese Application No. 2010-043533 mailed Mar. 4, 2014 (5 pgs).
Official Action and English translation from corresponding Japanese Application No. 201180010858.0 dated Jan. 6, 2014 (10 pgs.).
European extended Search Report from corresponding European Application No. 11747373.6 dated Mar. 3, 2014 (5 pgs).

* cited by examiner

ABSORBENT ARTICLE WITH PRESSED GROOVES OVERLYING A COMPRESSED REGION AND METHOD OF MANUFACTURING THE SAME

RELATED APPLICATION

This application is a 35 U.S.C. §371 national phase filing of International Patent Application No. PCT/JP2011/053940 filed Feb. 23, 2011, to which priority is claimed under 35 U.S.C. §120 and through which priority is claimed under 35 U.S.C. §119 to Japanese Patent Application No. 2010-043533, filed Feb. 26, 2010.

TECHNICAL FIELD

The present invention relates an absorbent article and a method of manufacturing the same.

BACKGROUND ART

Conventionally, there has been known a technique in which, in order to improve a capability to diffuse bodily (diffusibility) fluid all over the inside of an absorption layer, a pressed region in an arbitrary shape is formed by performing a pressing process (embossing process) to a topsheet and the absorption layer.

For example, there has been known a technique in which, after a surface embossment is formed by performing an embossing process to the absorbent article from a side facing to the topsheet, an absorber embossment is formed by performing the embossing process to the absorbent article from the side facing to the topsheet, with respect to the absorption layer within a range in which such a surface embossment has been formed (for example, see Patent Literature 1).

According to the above technique, the bodily fluid flowed in the surface embossment is absorbed from a side surface portion of the surface embossment, and then is shifted to the absorber embossment rapidly and effectively, thereby being able to be diffused along the absorber embossment.

CITATION LIST

Patent Literature

[PTL 1] Japanese Patent Unexamined Publication No. 2005-160702

SUMMARY OF INVENTION

However, the applicants found out that there is a problem in a case where the absorber embossment is formed by performing the embossing process to the absorbent article from the side facing to the topsheet, likewise the aforementioned technique.

In such case, the fiber density of the upper side in the thickness direction of the absorption layer is higher than that of the lower side thereof, so that diffusion is more promoted in the upper side as compared to the lower side in the thickness direction of the absorption layer, leading to the problem that the wetted area is undesirably increased in a skin contact surface side of the absorbent article.

Therefore, the present invention has been achieved in consideration of such circumstances, and an object thereof is to provide an absorbent article which is capable of reducing the wetted area in a skin contact surface side of the absorbent article by promoting more diffusion in the lower side than the upper side in the thickness direction of the absorption layer, and a method of manufacturing the absorbent article.

The first aspect of the present invention is summarized as an absorbent article including: a liquid-permeable topsheet; a liquid-impermeable backsheet; and an absorption layer arranged between the topsheet and the backsheet, wherein: a compressed region is formed by a compressing process in the absorption layer on a side facing to the backsheet; and a plurality of pressed grooves are formed by a pressing process in the absorption layer on a side facing to the topsheet, within a region opposed to the compressed region.

The second aspect of the present invention is summarized as a method of manufacturing an absorbent article including a liquid-permeable topsheet, a liquid-impermeable backsheet, and an absorption layer arranged between the topsheet and the backsheet, the method including: a step of forming a compressed region in the absorption layer by performing a compressing process to the absorbent article from a side facing to the backsheet; and a step of forming a plurality of pressed grooves within a region opposed to the compressed region in the absorption layer, by performing a pressing process to the absorbent article from a side facing to the topsheet.

As described above, according to the present invention, it is possible to provide an absorbent article which is capable of reducing the wetted area in a skin contact surface side of the absorbent article by promoting more diffusion in the lower side than the upper side in the thickness direction of the absorption layer, and a method of manufacturing the absorbent article.

DESCRIPTION OF EMBODIMENTS

First Embodiment of Present Invention

Figure 1:
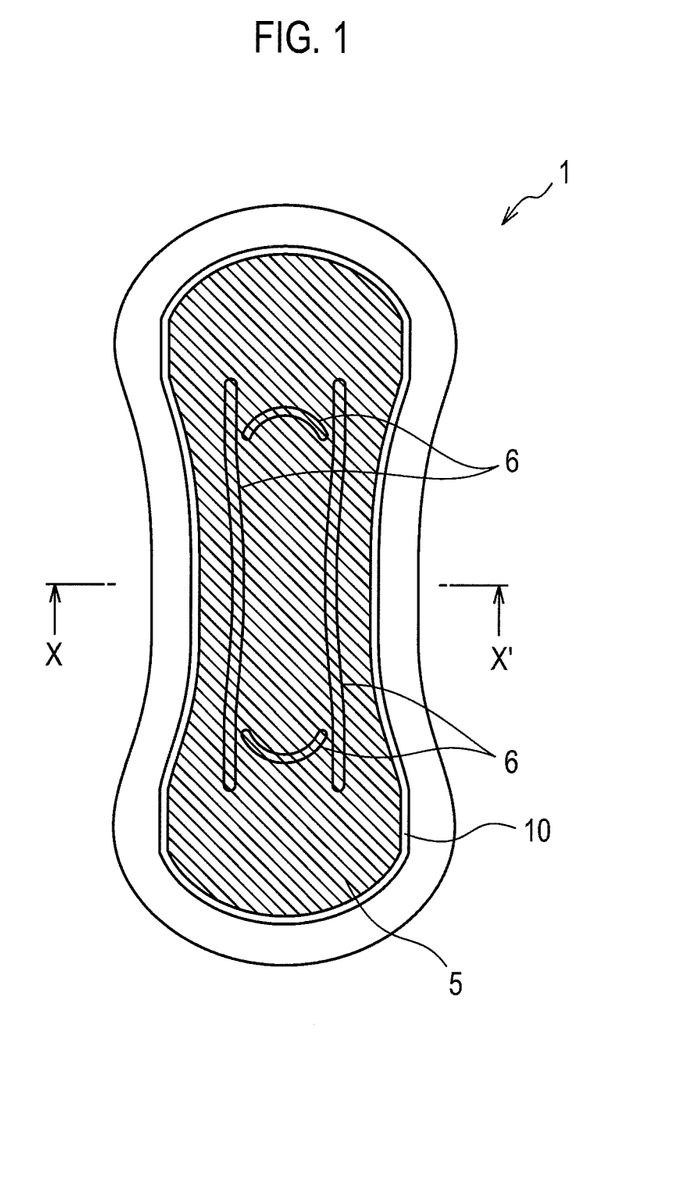
FIG. 1 is a plan view of an absorbent article as seen from a side facing to a topsheet, according to a first embodiment of the present application.
Figure 2:
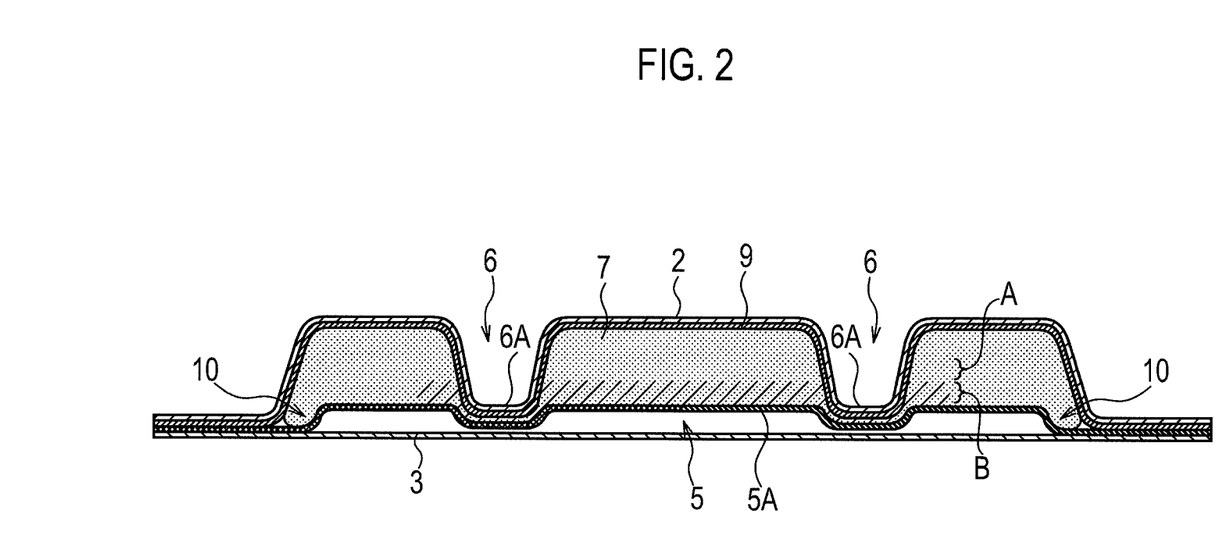
FIG. 2 is a cross-sectional view taken along the line X-X' of the absorbent article according to the first embodiment of the present invention.

With reference to FIGS. 1 and 2, an absorbent article 1 according to the first embodiment of the present invention is explained.

For example, an absorbent article 1 according to the present embodiment is a paper diaper, an incontinence pad, sanitary napkin, or the like.

The absorbent article 1 according to the present embodiment has a substantially vertically-elongated shape, as shown in FIGS. 1 and 2, and includes a topsheet 2, a backsheet 3, and an absorption layer 7.

The topsheet 2 is a liquid-permeable sheet provided in a skin contact surface side of the absorbent article 1 with respect to a wearer, and is configured from an air-through nonwoven cloth, a spun bond nonwoven cloth, or a porous film attached with a hydrophilizing agent, or a combination thereof.

The backsheet 3 is configured from a liquid-impermeable resin sheet provided on a clothing contact surface of the absorbent article 1 with respect to the wearer, and is configured from, for example, a liquid-impermeable film made from low-density polyethylene (LDPE) with a base weight of 15 $g/m^2$ to 40 $g/m^2$.

The absorption layer 7 is configured so as to absorb bodily fluid such as urine and menstrual blood, and is configured by sandwiching, for example, a deposited mixture of fluff pulp and superabsorbent polymer (SAP) by a liquid-diffusive sheet 9.

Specifically, the absorption layer 7 is formed by mixing superabsorbent polymer 8 into ground fluff pulp 7 between upper and lower layers of the liquid-diffusive sheet 9, which is configured from tissue paper or the like, and by sealing the upper and lower layers of the liquid-diffusive sheet 9 by joining the ends thereof together.

Further, instead of the liquid-diffusive sheet 9, a liquid-permeable sheet such as an air-through nonwoven cloth or a spun bond nonwoven cloth may be used.

Herein, a basis weight of the fluff pulp may be within a range of 100 $g/m^2$ to 550 $g/m^2$, which is assumed to give the wearer a comfortable feeling at the time of wearing, or may be within other range.

Further, the superabsorbent polymer is dispersed almost uniformly all over the absorption layer 7, and a basis weight of the superabsorbent polymer may be within a range of 0 $g/m^2$ to 400 $g/m^2$ or other range.

Yet further, the superabsorbent polymer is mixed with the fluff pulp uniformly, and a polymer ratio in the absorption layer 7 may be limited to approximately 45% by which concentration of the superabsorbent polymer hardly occurs.

Note that the superabsorbent polymer is made from well-known absorbent resin powder or the like.

Further, instead of uniform mixing of the fluff pulp and the superabsorbent polymer, a configuration of sandwiching a layer of the superabsorbent polymer between layers of the fluff pulp may be adopted.

Respective components of the above absorbent article 1 may be joined together by means of an appropriate joining method such as adhesion using generally-well-known hot-melt adhesive or welding using heat or supersonic waves.

Further, a side gather may be arranged on each of the right and left sides of a main body of the absorbent article 1 configured from the topsheet 2, the absorption layer 7, and the backsheet 3.

Further, a compressed region 5 (that is, a concave portion) is formed by a compressing process to the absorption layer on a side facing to the backsheet 3.

Herein, a surface of the compressed region 5 may be flat or may be provided with an embossment in an arbitrary shape.

Further, as shown in FIG. 1, the compressed region 5 may be formed almost all over the face on the backsheet 3 side of the absorption layer 7.

Yet further, on the side facing to the topsheet 2 of the absorption layer 7, a plurality of pressed grooves 6 (that is, embossment) are formed within a region opposed to the compressed region 5 by means of the pressing process.

These pressed grooves 6 may be an embossment in an arbitrary shape.

Figure 3:
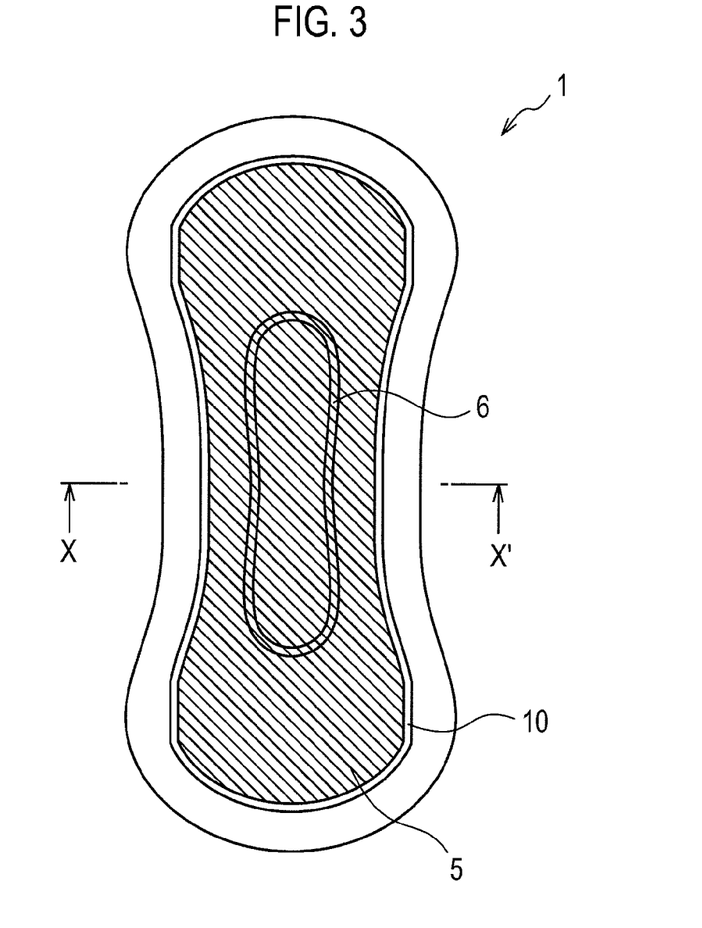
FIG. 3 is a plan view of the absorbent article as seen from the side facing to the topsheet, according to the first embodiment of the present invention.

Herein, as shown in FIG. 3, likewise a case where the pressed groove 6 having a closed shape such as a circular shape, an elliptical shape, or a polygon shape is formed within the region opposed to the compressed region 5, in a case as shown in FIG. 1, where the plurality of pressed grooves 6 are formed within the region opposed to the compressed region 5 when viewed from a cross-sectional view in the widthwise direction of the absorbent article 1, it is deemed that "the plurality of pressed grooves 6 are formed within the region opposed to the compressed region 5".

In the absorbent article 1 according to the present embodiment, as shown in FIG. 1, all of the plurality of pressed grooves 6 are formed within the region opposed to the compressed region 5.

In the absorbent article 1 according to the present embodiment, as shown in FIG. 2, bottom faces 6A of the pressed grooves 6 are disposed closer to the backsheet 3 than a bottom face 5A of the compressed region 5.

Specifically, in the absorbent article 1 according to the present embodiment, the bottom faces 6A of the pressed grooves 6 are formed in a manner to project from the bottom face 5A of the compressed region 5 towards the backsheet 3.

With such a configuration, the pressed grooves 6 can be deeply formed, thereby being able to store bodily fluid temporarily.

Further, in the absorbent article 1 according to the present embodiment, the bottom face 5A of the compressed region 5 may be formed so as to approach the topsheet 2 as extending towards the outer edge of the compressed region 5.

With such a configuration, the fiber density of the absorption layer 7 increases as approaching the outer edge of the compressed region 5, so that the bodily fluid can be easily guided in the thickness direction of the absorbent article 1.

Further, in the absorbent article 1 according to the present embodiment, as shown in FIG. 2, a gradient of the fiber density is formed in the thickness direction of the absorption layer 7, and the fiber density of a region A on the side facing to the topsheet 2 in the thickness direction of the absorption layer 7 may be lower than that of a region B on the side facing to the backsheet 3 in the thickness direction of the absorption layer 7.

Further, in the absorbent article 1 according to the present embodiment, as shown in FIG. 2, the fiber density of the bottom faces 6A of the pressed grooves 6 may be higher than that of the region A on the side facing to the topsheet 2 in the thickness direction of the absorption layer 7 and that of the region B on the side facing to the backsheet 3 in the thickness direction of the absorption layer 7.

Yet further, in the absorbent article 1 according to the present embodiment, as shown in FIGS. 1 and 2, an uncompressed region 10 not subjected to the compressing process may be formed outside the compressed region 5, along the outer circumference thereof.

Figure 4:
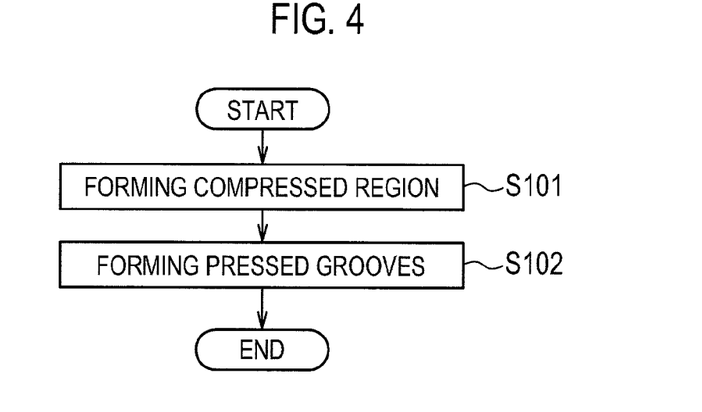
FIG. 4 is a flowchart for illustrating a method of manufacturing the absorbent article according to the first embodiment of the present invention.

Next, with reference to FIG. 4, part of the method of manufacturing the absorbent article 1 according to the present embodiment is explained.

Hereinafter, the method of manufacturing the absorbent article 1 according to the present embodiment is explained with a focus on a method of producing the compressed region 5 and the pressed grooves 6 described above.

As far as the other methods, the existing method can be used.

As shown in FIG. 4, in step S101, the compressed region 5 is formed in the absorption layer 7 by performing the compressing process to the absorbent article 1 from the side facing to the backsheet 3.

In step S102, the topsheet 2 is overlapped from the skin contact surface side, with the absorption layer 7, and the pressing process is performed to the absorbent article 1 from the side facing the topsheet 2 so that in the absorption layer 7, the plurality of pressed grooves 6 are formed within a region opposed to the compressed region 5.

Thereafter, the backsheet 3 is laminated on the opposite side of the side facing to the topsheet 2 of the absorption layer 7, thereby joining the periphery of the topsheet 2 and the periphery of the backsheet 3 together.

Hereinafter, with reference to (Table 1), results of an evaluation test using following absorbent articles are explained.

Example 1

Absorbent article (with a size of 150 mm×150 mm) according to the present embodiment, with the use of the absorption layer 7 configured only from fluff pulp with a basis weight of 400 g/m²

Comparative Example 1

Absorbent article (with a size of 150 mm×150 mm) with the use of the absorption layer 7 configured only from fluff pulp with a basis weight of 400 g/m², in which after formation of the compressed region 5 to the absorption layer 7 on the side facing to the topsheet 2, the plurality of pressed grooves 6 are formed to the absorption layer 7 on the side facing to the topsheet 2

Example 2

Absorbent article (with a size of 150 mm×150 mm) according to the present embodiment, with the use of the absorption layer 7 configured from fluff pulp with a basis weight of 400 g/m² and superabsorbent polymer with a basis weight of 266 g/m²

Comparative Example 2

Absorbent article (with a size of 150 mm×150 mm) with the use of the absorption layer 7 configured from fluff pulp with a basis weight of 400 g/m² and superabsorbent polymer with a basis weight of 266 g/m², in which after formation of the compressed region 5 to the absorption layer 7 on the side facing to the topsheet 2, the plurality of pressed grooves 6 are formed to the absorption layer 7 on the side facing to the topsheet 2

In this evaluation test, artificial bodily fluid (artificial urine) was dripped onto each of the absorbent articles to measure a diffusion area of the artificial bodily fluid in the side facing to the topsheet 2 of each of the absorbent articles.

Note that used as artificial bodily fluid was an aqueous solution containing 2% by weight of urea, 0.8% by weight of sodium chloride, 0.08% by weight of magnesium sulfate heptahydrate, and 0.03% by weight of calcium chloride dihydrate.

TABLE 1

| | formation position of compressed region 5 | drip volume (ml) | configuration of absorption layer 7 | diffusion area on side facing to topsheet 2 (mm²) | diffusion area difference in a case of setting 1 to examples |
|---|---|---|---|---|---|
| Example 1 | entire surface of absorption layer | 10 | only fluff pulp | 2691 | 1 |
| Comparative Example 1 | | | | 4750 | 1.8 |
| Example 2 | | | superabsorbent polymer + fluff pulp | 3622 | 1 |
| Comparative Example 2 | | | | 5460 | 1.5 |

Herein, as is clear from (Table 1), diffusion areas of the artificial bodily fluid on the side facing to the topsheet 2 of the absorption layer 7 in (Comparative Example 1) and (Comparative Example 2) are 1.5 times and 1.8 times larger than diffusion areas of the artificial bodily fluid on the side facing to the topsheet 2 of the absorption layer 7 in (Example 1) and (Example 2), respectively.

Therefore, the absorbent articles used in (Comparative Example 1) and (Comparative Example 2) have a larger diffusion area of the artificial bodily fluid on the side facing to the topsheet 2 of the absorption layer 7, as compared to the absorbent articles used in (Example 1) and (Example 2), that is, the absorbent article 1 according to the present embodiment.

Thus, the absorbent article 1 according to the present embodiment can further reduce an uncomfortable feeling to the skin after absorption of the bodily fluid, as compared to the absorbent articles used in (Comparative Example 1) and (Comparative Example 2).

Specifically, according to the absorbent article 1 of the present embodiment, after formation of the compressed region 5 to the absorption layer 7 on the side facing to the backsheet 3, the pressed grooves 6 are formed to the absorption layer 7 on the side facing to the topsheet 2, so that the fiber density in the region B on the side facing to the backsheet 3 in the thickness direction of the absorption layer 7 can be made higher than that in the region A on the side facing to the topsheet 2 in the thickness direction of the absorption layer 7.

Therefore, diffusion in the region B on the side facing to the backsheet 3 in the thickness direction of the absorption layer 7 can be enhanced more than that in the region A on the side facing to the topsheet 2 in the thickness direction of the absorption layer 7, so that a wetted area can be reduced in the skin contact surface side of the absorbent article 1.

Further, according to the absorbent article 1 of the present embodiment, a gradient of the fiber density can be formed in the thickness direction of the absorption layer 7 as a single layer, so that as compared to a case using a plurality of absorption layers with different fiber densities, processing costs and adjustment parts can be reduced, thereby achieving easier production at lower cost.

Yet further, according to the absorbent article 1 of the present embodiment, the pressed grooves 6 can be formed within a region of the absorption layer 7 which is thinned by the existence of the compressed region 5 formed to the absorption layer 7 on the side facing to the backsheet 3, so that the compressed regions 6 can be formed and retained with accuracy and ease.

Further, according to the absorbent article 1 of the present embodiment, a configuration is made so as to form the pressed regions 6 after formation of the compressed region 5 in the absorption layer 7, so that the pressed grooves 6 are formed with a higher fiber density as compared to a case of the absorption layer 7 not provided with the compressed region 5.

Therefore, the topsheet 2 can be melt-solidified while the bottom faces 6 of the pressed grooves 6 are in a denser condition, so that a pressure bonding strength can be increased in the bottom faces 6A of the pressed grooves 6.

As a result, a tear of the topsheet 2 can be reduced within the bottom faces 6A of the pressed grooves, thereby being able to reduce an escape of the superabsorbent polymer from the bottom faces of the pressed grooves 6.

Yet further, according to the absorbent article 1 of the present embodiment, the uncompressed region 10 is formed along the outer circumference of the compressed region 5, thereby being able to restrain diffusion of the bodily fluid towards the outside of the compressed region 5.

Specifically, this slows the reaching of bodily fluid to the ends of the absorption layer 7.

Modification 1

Figure 5:
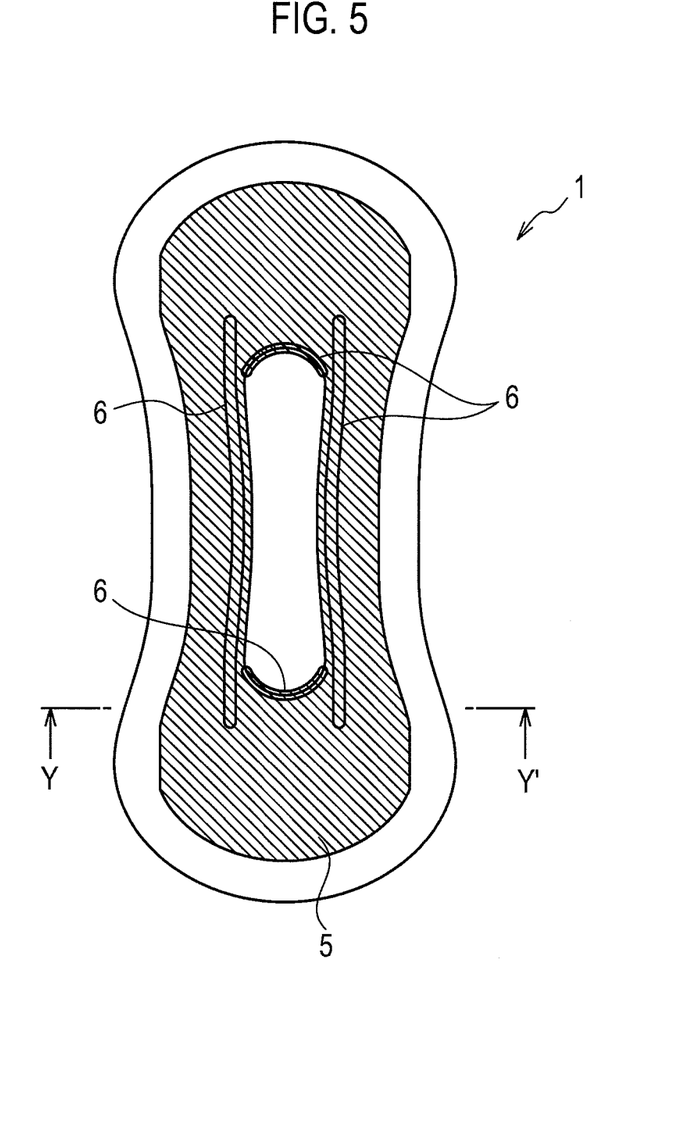
FIG. 5 is a plan view of an absorbent article as seen from a side facing to a topsheet, according to a first modification of the present invention.
Figure 6:
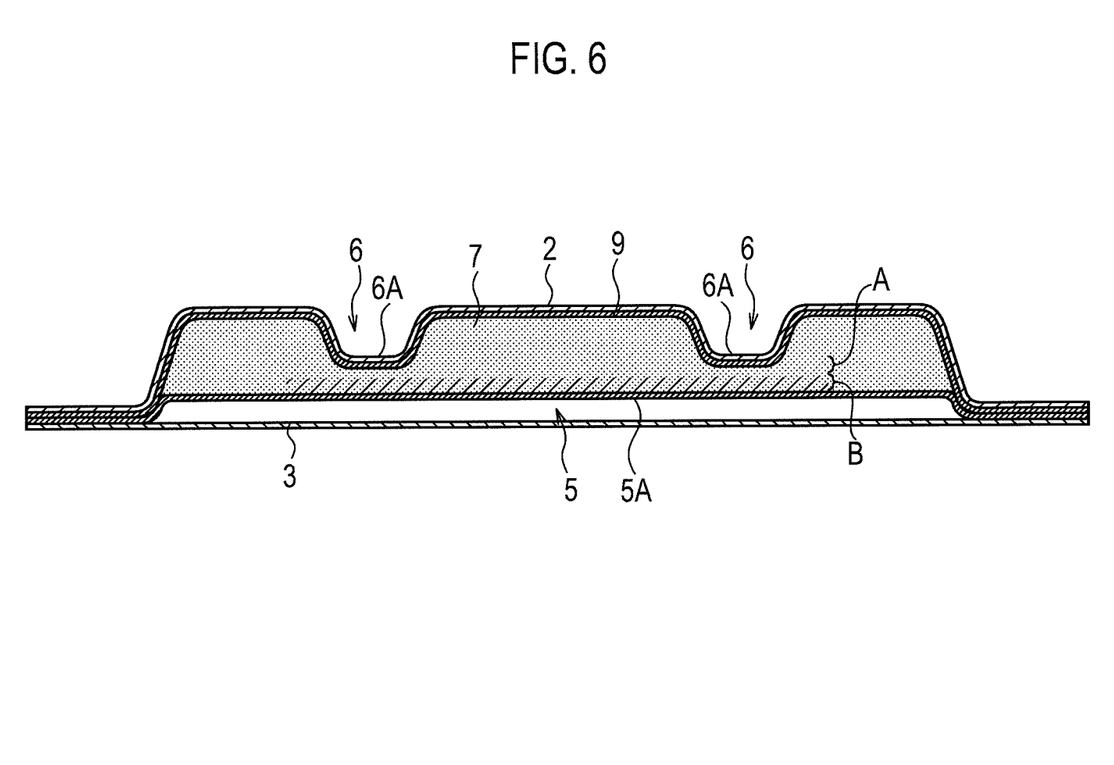
FIG. 6 is a cross-sectional view taken along the line Y-Y' of the absorbent article according to the first modification of the present invention.

With reference to FIGS. 5 and 6, an absorbent article 1 according to the first modification of the present invention is explained.

Hereinafter, the absorbent article 1 according to this first modification is explained with a focus on differences from the absorbent article 1 according to the first embodiment described above.

As shown in FIGS. 5 and 6, in the absorbent article 1 according to this first modification, a compressed region 5 may be formed along part of the surface on the side facing to a backsheet 3 of an absorption layer 7, for example, along a region into which the bodily fluid is desirably diffused.

For example, as shown in FIGS. 5 and 6, in the absorbent article 1 according to this first modification, the compressed region 5 is not formed in the central region of the surface on the side facing to the backsheet 3 of the absorption layer 7. This makes it easy to diffuse the bodily fluid into an outer region of the absorption layer 7, so that the entire absorption layer 7 can be used without any waste.

As shown in FIGS. 5 and 6, the absorbent article 1 according to the first modification is not provided with an uncompressed region 10 which is formed along the outer circumference of the compressed region 5 in the absorbent article 1 according to the above first embodiment.

Modification 2

Figure 7:
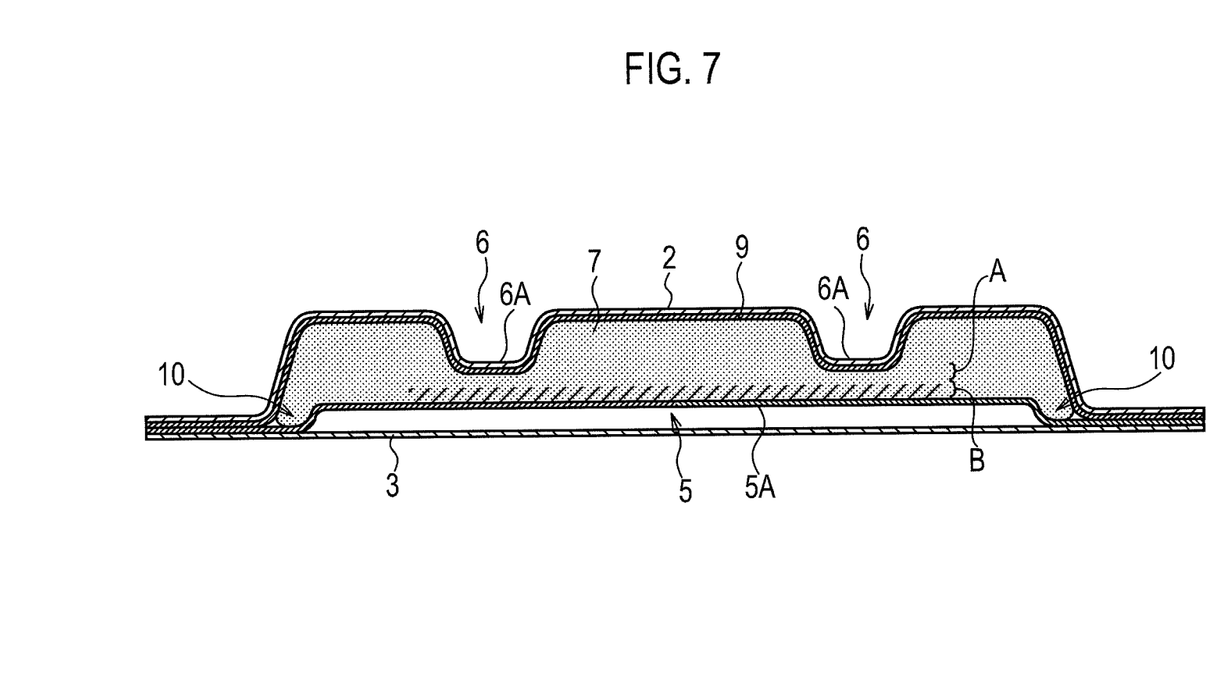
FIG. 7 is a cross-sectional view taken along the line X-X' of an absorbent article according to a second modification of the present invention.

With reference to FIG. 7, an absorbent article 1 according to the second modification of the present invention is explained.

Hereinafter, the absorbent article 1 according to this second modification is explained with a focus on differences from the absorbent article 1 according to the first embodiment described above.

As shown in FIG. 7, in the absorbent article 1 according to this second modification, bottom faces 6A of pressed grooves 6 are disposed so as not to reach a bottom face 5A of a compressed region 5.

Note that the bottom faces 6A of the pressed grooves 6 may be arranged so as to reach the bottom face 5A of the pressed region 5.

Modification 3

Figure 8:
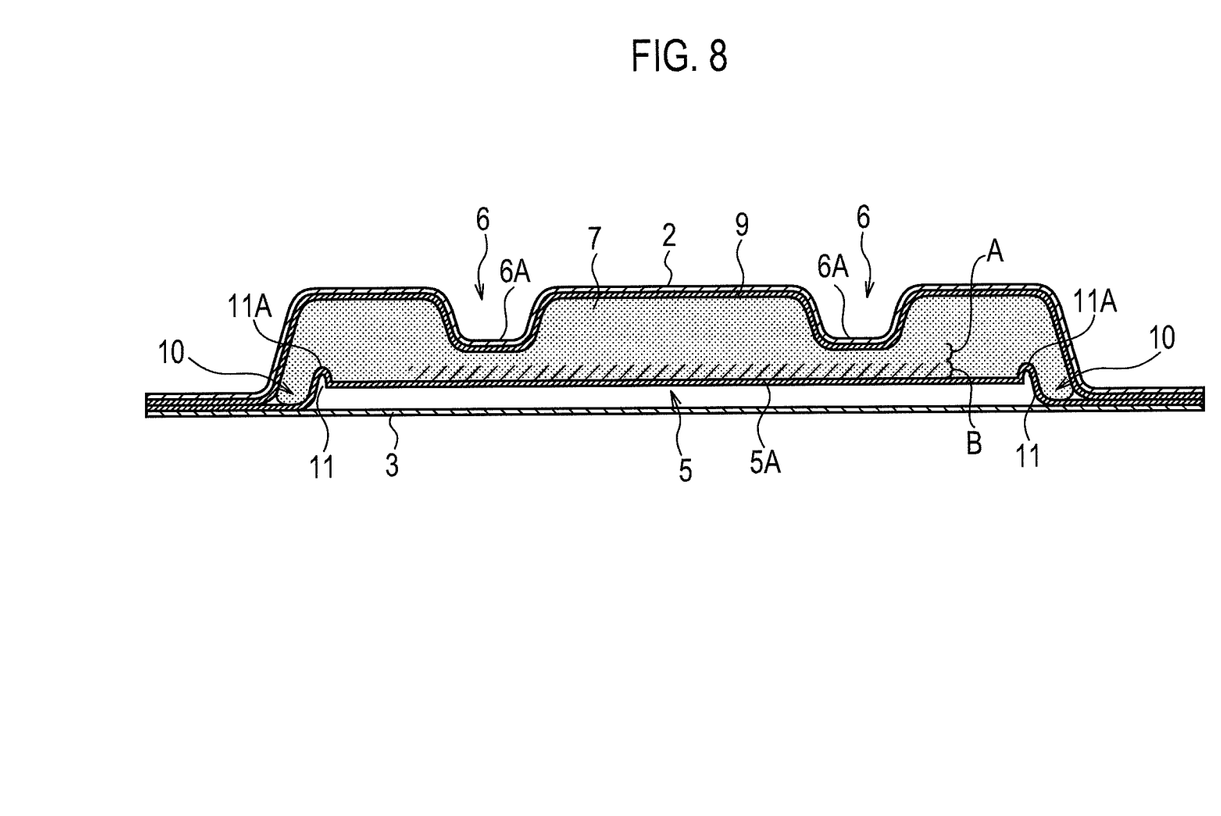
FIG. 8 is a cross-sectional view taken along the line X-X' of an absorbent article according to a third modification of the present invention.

With reference to FIG. 8, an absorbent article 1 according to the third modification of the present invention is explained.

Hereinafter, the absorbent article 1 according to this third modification is explained with a focus on differences from the absorbent article 1 according to the first embodiment described above.

As shown in FIG. 8, in the absorbent article 1 according to this third modification, an outer edge portion 11 is formed in the vicinity of the outer edge of the compressed region 5.

Herein, as shown in FIG. 8, a bottom face 11A of the outer edge portion 11 is arranged closer to a topsheet 2 than a bottom face 5A of the compressed region 5.

With such a configuration, diffusion of the bodily fluid in the outer direction of the absorption layer 7 can be restrained by the outer edge portion 11 positioned in front of the end of the absorption layer 7, thereby being able to guide the bodily fluid so as to diffuse in the circumferential direction along the outer edge portion 11.

As described above, the present invention has been described in detail by using the above-described embodiment.

However, it is apparent to those skilled in the art that the present invention is not limited to the embodiment described in this description.

The present invention can be modified and changed without departing from the gist and the scope of the present invention defined by the appended claims.

Therefore, the description is aimed at illustration and explanation of the present invention, and does not have any meaning which limits the present invention.

The entire contents of Japanese Patent Application Laid-open No. 2010-043533 (filed on Feb. 26, 2010) are incorporated in the present specification by reference.

INDUSTRIAL APPLICABILITY

As described above, according to the present invention, it is possible to provide an absorbent article which is capable of reducing a wetted area in a skin contact surface side of the absorbent article by promoting more diffusion in a lower side than a upper side in a thickness direction of an absorption layer, and a method of manufacturing the absorbent article.

DESCRIPTION OF THE NUMERALS

1 . . . absorbent article, 2 . . . topsheet, 3 . . . backsheet, 5 . . . compressed region, 6 . . . pressed groove, 7 . . . absorption layer, 9 . . . liquid-diffusive sheet, 10 . . . uncompressed region, 11 . . . outer edge portion.

The invention claimed is:

1. An absorbent article comprising:
a liquid-permeable topsheet;
a liquid-impermeable backsheet; and
an absorption layer arranged between the topsheet and the backsheet, wherein:
a compressed region is formed by a compressing process in the absorption layer on a side facing to the backsheet;
a plurality of pressed grooves are formed by a pressing process in the absorption layer on a side facing to the topsheet, within a region opposed to the compressed region;

a bottom face of the compressed region is formed so as to be closer to the topsheet near outer edges of the compressed region; and a fiber density of the absorption layer increases near said outer edges of the compressed region.

2. The absorbent article according to claim 1, wherein bottom faces of the pressed grooves are arranged closer to the backsheet than a bottom face of the compressed region.

3. The absorbent article according to claim 1, wherein the pressed grooves are formed after formation of the compressed region.

4. The absorbent article according to claim 1, wherein an uncompressed region not subjected to the compressing process is formed in the absorption layer along an outer circumference of the compressed region, on an outer side of the compressed region.

5. The absorbent article according to claim 4, wherein:

an outer edge portion is formed in the absorption layer in a vicinity of an outer edge of the compressed region; and a bottom face of the outer edge portion is arranged closer to the topsheet than a bottom face of the compressed region.

6. A method of manufacturing an absorbent article including a liquid-permeable topsheet, a liquid-impermeable backsheet, and an absorption layer arranged between the topsheet and the backsheet, the method comprising:

a step of forming a compressed region in the absorption layer by performing a compressing process to the absorbent article from a side facing to the backsheet; and a step of forming a plurality of pressed grooves within a region opposed to the compressed region in the absorption layer, by performing a pressing process to the absorbent article from a side facing to the topsheet, wherein a bottom face of the compressed region is formed so as to be closer to the topsheet near outer edges of the compressed region; and a fiber density of the absorption layer increases near said outer edge of the compressed region.

\* \* \* \* \*